# (12) United States Patent
Cervantes et al.

(10) Patent No.: US 7,517,140 B2
(45) Date of Patent: Apr. 14, 2009

(54) TECHNIQUES FOR PRECISION TESTING OF THERMAL INTERFACE MATERIALS

(75) Inventors: Joseph A. Cervantes, Mountain View, CA (US); Sridhar V. Machiroutu, Fremont, CA (US); Shawn McEuen, Portland, OR (US); Joshua T. Linden-Levy, Portland, OR (US); Robert W. Wolcott, Newberg, OR (US)

(73) Assignee: Intel Corporation, Santa Clara, CA (US)

( * ) Notice: Subject to any disclaimer, the term of this patent is extended or adjusted under 35 U.S.C. 154(b) by 160 days.

(21) Appl. No.: 11/535,915

(22) Filed: Sep. 27, 2006

(65) Prior Publication Data

US 2008/0075137 A1    Mar. 27, 2008

(51) Int. Cl.
*G01K 3/00* (2006.01)
*G01N 25/00* (2006.01)

(52) U.S. Cl. .................. 374/7; 374/184; 374/166; 374/112; 374/29

(58) Field of Classification Search ............... 374/51, 374/43, 29, 30, 44, 112, 184; 702/136
See application file for complete search history.

(56) References Cited

U.S. PATENT DOCUMENTS

| | | | | |
|---|---|---|---|---|
| 3,263,485 A | * | 8/1966 | Parviz | 374/44 |
| 3,521,476 A | * | 7/1970 | Day | 374/44 |
| 3,733,887 A | * | 5/1973 | Stanley et al. | 374/44 |
| 5,940,784 A | * | 8/1999 | El-Husayni | 702/130 |
| 6,116,777 A | * | 9/2000 | Pause | 374/43 |
| 6,142,662 A | * | 11/2000 | Narh et al. | 374/44 |
| 6,331,075 B1 | * | 12/2001 | Amer et al. | 374/44 |
| 2003/0072349 A1 | * | 4/2003 | Osone et al. | 374/43 |
| 2005/0058178 A1 | * | 3/2005 | Shih et al. | 374/51 |
| 2006/0045165 A1 | * | 3/2006 | Chan et al. | 374/43 |

FOREIGN PATENT DOCUMENTS

FR    2643717 A1 *  8/1990

\* cited by examiner

*Primary Examiner*—Gail Verbitsky
*Assistant Examiner*—Mirellys Jagan
(74) *Attorney, Agent, or Firm*—Kacvinsky LLC

(57) ABSTRACT

Techniques for precision testing of thermal interface materials are described. An apparatus may include multiple anvils each having multiple sensors disposed along its axis. A thermal interface material may be disposed between the anvils. A control module may be communicatively coupled to said sensors and arranged to receive temperature readings from the multiple sensors to form a temperature gradient, determine a surface temperature for each anvil based on the temperature gradient, determine a heat flux through the thermal interface material based on the surface temperature, and determine a resistance value for the thermal interface material based on the heat flux. Other embodiments are described and claimed.

17 Claims, 5 Drawing Sheets

TECHNIQUES FOR PRECISION TESTING OF THERMAL INTERFACE MATERIALS

BACKGROUND

Electronic devices are continuing to increase features while reducing form factors. As a result, electronic devices are becoming densely packed with components and devices, which leaves little room for cooling. Various cooling techniques are typically employed, such as using cooling fans, heat pipes, heat exchangers, heat sinks, air, water, and so forth. In most cases, various thermal interface materials (TIM) are used to connect or couple the thermal solution to the hot component. A TIM may enhance the thermal contact between the thermal solution and the hot component. Consequently, the ability of a TIM to efficiently transfer the thermal energy from the hot component to the thermal solution may be critical to the total thermal solution design. Accordingly, there may be a substantial need for precise measurement techniques to measure the performance of various TIM.

DETAILED DESCRIPTION

Figure 1:
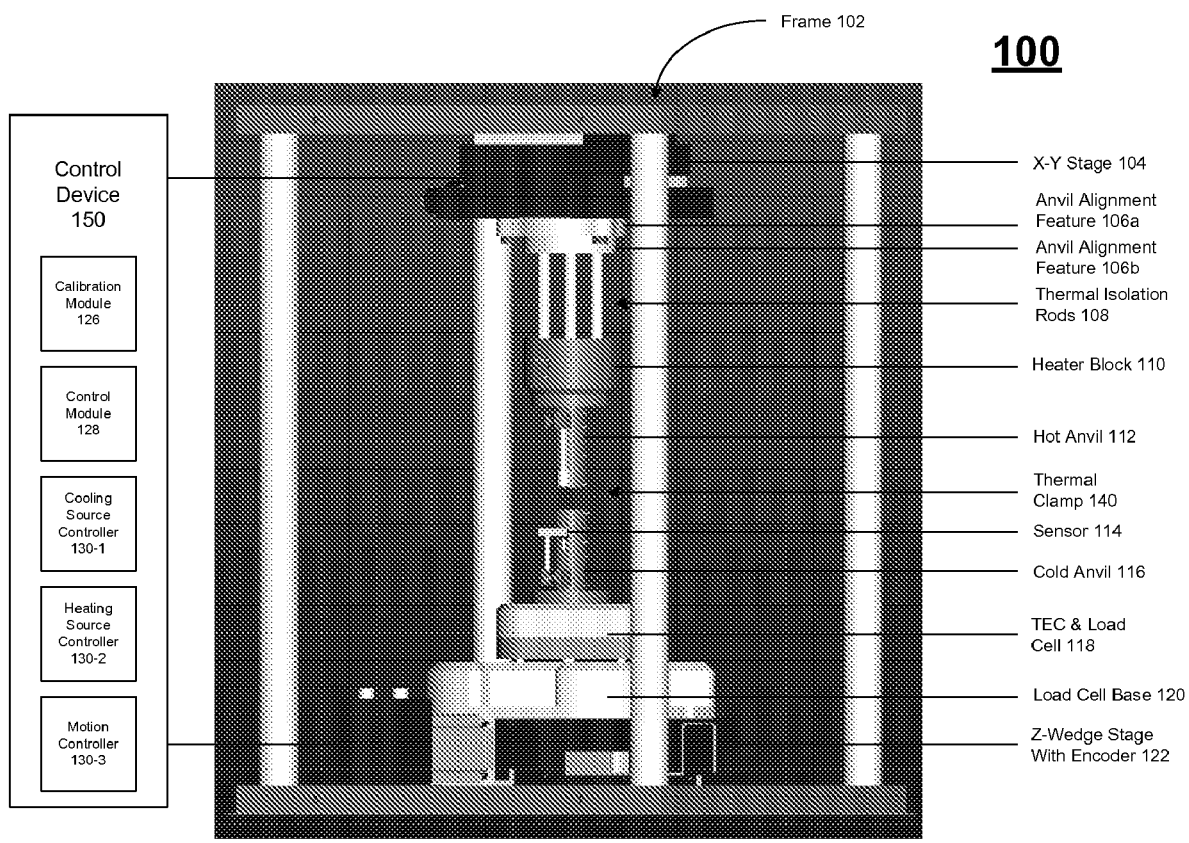
FIG. 1 illustrates one embodiment of a precision material tester.

Various embodiments as described herein may comprise one or more elements. An element may comprise any structure arranged to perform certain operations. Each element may be implemented as hardware, software, or any combination thereof, as desired for a given set of design parameters or performance constraints. Although an embodiment may be described with a limited number of elements in a certain topology by way of example, the embodiment may include more or less elements in alternate topologies as desired for a given implementation. It is worthy to note that any reference to "one embodiment" or "an embodiment" means that a particular feature, structure, or characteristic described in connection with the embodiment is included in at least one embodiment. The appearances of the phrase "in one embodiment" in various places in the specification are not necessarily all referring to the same embodiment.

Various embodiments may be generally directed to techniques for precisely measuring various materials, such as one or more types of TIM. In some embodiments, for example, this may be accomplished using a precision material tester. In one embodiment, for example, the precision material tester may be implemented in accordance with one or more ASTM standards, such as the ASTM standard titled "Standard Test Method for Thermal Transmission Properties of Thin Thermally Conductive Solid Electrical Insulation Materials," ASTM D-5470-01, 1999 (the "ASTM Standard"), as well as its progeny, successors and variants. In various embodiments, the precision material tester may be capable of providing more accurate measurements of various thermal materials, such as various TIM. In some embodiments, for example, the precision material tester may provide accurate measurements for various TIM at or below 0.1 $C.cm^2/W$. In this manner, thermal solutions may be more precisely designed to improve cooling and heat reduction performance.

Precision testing of various TIM may be important for a number of different applications. For example, notebook computers are typically densely packed with components thereby creating cooling problems. This problem is further exacerbated when notebook computers have smaller form factors, which tend to limit the thermal solution options for the system components that must be cooled in order to get any appreciable performance. For example, some notebooks utilizing Intel® Centrino® mobile technology may use remote heat exchange (RHE) techniques to perform dedicated active cooling of high-power components. An example of a RHE technique may include using a heat pipe to transport the thermal energy from a hot component such as a processor (e.g., a bare-die Pentium® M processor) to a location where a larger fan and heat exchanger can be used. The efficiency of heat draw by the heat pipe from the processor depends on the quality of thermal contact between the attach block and the processor. In general, the lower the thermal contact resistance, the lower the temperature drop from the silicon transistor to the ambient.

Even in a direct contact, however, the processor and the attach block do not transfer heat efficiently, because the quality of contact between two non-conforming solid surfaces is typically poor. A TIM may therefore be inserted between the processor and the attach block in order to enhance the thermal contact between the two surfaces. Under mechanical pressure, the soft TIM conforms to the microscopic surface contours of the adjacent solid surfaces and increases the microscopic area of contact between the thermal solution surface (block) and the silicon die surface (processor) and therefore reduces the temperature drop across this contact. The quality of the contact between the processor and the attach block, or TIM performance, depends on the quality of the thermal conduction through the TIM and the quality of contact between the TIM and the two surfaces. Consequently, a precise material tester capable of providing precise measurements of TIM performance may be useful to improve overall thermal solution designs for notebooks and other devices.

A precision material tester may provide several advantages over conventional material testers. For example, conventional material testers typically have poor load control, poor mating jaw alignment, and are relatively under-instrumented. A precision material tester, however, increases the number and quality of sensors thereby allowing more accurate estimates of the TIM performance. Because the precision material tester uses more temperature sensors in the thermal clamp, the estimate of the clamp surface temperature is more accurate that other ASTM-based devices. In another example, conventional material testers typically determines heat flux (Q) at the TIM interfaces by explicitly measuring the power input to the heater at the base of the hot jaw of the thermal clamp, or alternatively, by using a reference calorimeter in the jaw assembly. A precision material tester, however, estimates the heat flux from the temperature gradient established in the clamp jaw during a given test. Given the more precise temperature gradient measured by the increased number and quality of sensors, the heat flux may be more precisely determined from the temperature gradient.

In one embodiment, for example, an apparatus such as a precision material tester may include multiple anvils each having multiple sensors disposed along its axis. A thermal interface material may be disposed between the anvils. A control module may be communicatively coupled to the sensors, and arranged to receive temperature readings from the multiple sensors to form a temperature gradient, determine a surface temperature for each anvil based on the temperature gradient, determine a heat flux through the thermal interface material based on the surface temperature, and determine a resistance value for the thermal interface material based on the heat flux. Other embodiments are described and claimed.

FIG. 1 illustrates one embodiment of a precision material tester 100. Precision material tester 110 may be used to measure various materials, such as one or more types of TIM. Examples of TIM suitable for measurement by precision material tester 100 may include, but are not necessarily limited to, various types of greases (e.g., AlNl, Ag, ZnO and silicon oil), various types of gels (e.g., Al, Ag, silicone oil and olefin), various types of phase change materials (e.g., polyolefins, epoxies, polyesters, acrylics, BN, alumina, Al and carbon nanotubes), various types of phase change metallic alloys (e.g., pure In, In/AG, Sn/Ag/Cu and In/Sn/Bi), various types of solders (e.g., pure In, In/AG, Sn/Ag/Cu and In/Sn/Bi), and so forth. It may be appreciated that these are merely some examples, and precision material tester 100 may be used to test any type of material suitable for use in thermal solution designs. The embodiments are not limited in this context.

As shown in FIG. 1, precision material tester 100 may comprise an ASTM-based TIM tester having multiple elements, such as a frame 102, an X-Y stage 104, anvil alignment features 106a, 106b, thermal isolation rods 108, a heater block 110, a hot anvil 112, a sensor 114, a cold anvil 116, a thermoelectric cooler (TEC) and load cell 118, a load cell base 120, a Z-wedge stage with encoder 122, and a control device 150. Control device 150 may include a control module 128 and one or more controllers 130-1-m. Precision material tester 100 as shown in FIG. 1, however, may include more or less elements, and is not necessarily limited to the elements shown in FIG. 1.

In various embodiments, the elements of precision material tester 100 may be categorized into four major groups of components: (1) mechanical elements; (2) controllers; (3) sensing and data acquisition components; and (4) control module. For example, the mechanical elements may include a thermal clamp 140 having anvils 112, 116 formed as corresponding jaws and instrumented with multiple thermistors, a heat source such as heater block 110, a cooling source such as TEC and load cell 118, one or more computer controlled positioning stages with position and force feedback such as X-Y stage 104 and Z-wedge stage with encoder 122, and a frame and safety enclosure such as frame 102.

In various embodiments, precision material tester 100 may be controlled using one or more controllers 130-1-m, where m may be any positive integer. In one embodiment, for example, precision material tester 100 may include at least three controllers, including a cooling source controller 130-1, a heating source controller 130-2, and a motion controller 130-3. The temperature controllers 130-1, 130-2 maintain the temperature of the bases of anvils 112, 116 of thermal clamp 140. Motion controller 130-3 controls movement for the dynamic jaws (e.g., anvils 112, 116) of thermal clamp 140, and when the clamp is closed, the clamping force imparted to the tested material (e.g., a TIM).

In various embodiments, precision material tester 100 utilizes multiple sensors for measuring temperature, force, and distance. In one embodiment, for example, anvils 112, 116 may be implemented as copper rods, with each copper rod having multiple sensors installed along its axis. In one embodiment, for example, anvils 112, 116 may be implemented with six thermistors installed at equally spaced intervals along the axis of each copper rod. The thermistors may be used to measure the temperature gradient or profile along the copper rods of anvils 112, 116 while a test is being conducted. TEC and load cell 118 is located at the base of cool anvil 116 of thermal clamp 140, and measures a clamping load on the TIM under test. An inductive position sensor 114, located at the interface of the two clamping anvils 112, 116, measures the thickness of the TIM under test. Signals from the thermistors are sampled at fixed time intervals by a data logger. In one embodiment, for example, the data logger may be implemented as an Agilent Model 34970A data logger. Signals from TEC and load cell 118 and inductive position sensor 114 are sampled using a sensor monitor that may be implemented using a computer based analog-to-digital (A/D) card. The data logger and computer based A/D card may be implemented, for example, as part of control device 150 as described in more detail with reference to FIG. 3.

In various embodiments, control device 150 may control operations for precision material tester 100. Control device 150 may comprise a processing system having a processor and memory that may be used to execute a control module 128 for precision material tester 100. For example, the control module 128 may allow the user set test parameters, initiate a test, and monitor the progress of a test. While a test is in progress, the control module 128 automatically maintains the test parameters supplied by the user, collects data, performs real time measurement and analysis, stores relevant test data on a computer hard disk, and performs other control and management operations as desired for a given implementation of precision material tester 100.

In general operation, precision material tester 100 may be initialized and "warmed up" to operating temperatures. Anvils 112, 116 are heated and cooled, respectively, and are allowed to reach a steady state temperature. Once precision material tester 100 has been brought to the appropriate operating temperatures, a material such as a TIM is loaded into precision material tester 100 and is clamped by the co-planar surfaces of anvils 112, 116 with a force as specified by the user. Once the specified load has been attained, heater block 110 heats hot anvil 112 while TEC and load cell 118 cools cold anvil 116. Once the temperatures of the bases of anvils 112, 116 are set to and maintained at the operating temperatures specified by the user, control device 150 may begin data acquisition operations. Data is collected from the thermistors embedded along the axis of anvils 112, 116, processed, and displayed at a predefined interval (e.g., 3 second intervals). Data may be collected throughout the thermal transient period. The data use to determine the thermal resistance of the material, however, is typically limited to the data collected after precision material tester 100 has reached a steady state. Using the information collected through the thermistors inserted into anvils 112, 116, the control module 128 may calculate temperature gradients for anvils 112, 116, surface temperatures for anvils 112, 116 from the temperature gradients, heat flux through anvils 112, 116 from the surface temperatures, and a thermal resistance for the tested TIM. Parameters for temperature, position, load, and calculated values are stored to a computer hard disk at periodic intervals (e.g., every minute). When precision material tester 100 is in a clamped position and has reached a steady state, the user may decide to terminate the test.

Once the temperature at the interface of each block is measured, the heat flux through the TIM may be measured. TIM resistance is considered one important measure of TIM performance. The heat flux may be used to calculate a TIM resistance value for a given TIM in accordance with Equation (1) as follows:

$$\theta_{TIM} = (T_{hot,int} - T_{cold,int})P \qquad \text{Equation (1)}$$

where P is the power (heat flux) conducted through the TIM, $T_{hot,int}$ is the temperature of the TIM interface on the hot side and $T_{cold,int}$ is the temperature of the TIM interface at the cold side.

In various embodiments, precision material tester 100 may be capable of more precisely measuring a TIM resistance ($\theta_{TIM}$) for various TIM. In some cases, for example, precision material tester 100 may be capable of providing accurate measurements for various TIM at or below 0.1 C.cm²/W. This level of accuracy may be achieved due to one or more innovative features used in the design, assembly or implementation of precision material tester 100, as described in more detail below.

In one embodiment, for example, precision material tester 100 may provide improved measurements by utilizing a higher number of sensors to measure temperature, force and distance for precision material tester 100. As previously described, each anvil 112, 116 may be implemented using a copper rod having multiple thermistors installed at equally spaced intervals along its axis. Although any number of thermistors may be used, a larger number of thermistors may provide more accurate readings and reduced errors. In one embodiment, for example, six thermistors may be used per axis to measure the temperature gradient or profile along each copper rod while a test is being conducted. The temperature gradient may be used to extrapolate surface temperatures for anvils 112, 116. Consequently, the higher temperature sensor count allows a more precise measurement of the surface temperatures by providing a higher level of error information. Accordingly, a more precise measurement of surface temperatures improves the accuracy of the ultimate thermal resistance measurement.

In addition to increasing the number of sensors, precision material tester 100 may also implement a higher quality sensor for cold anvil 116. In one embodiment, for example, sensor 114 may be implemented using an inductive sensor for distance measurement. Precision material tester 100 may use inductive sensor 114 to perform a high precision localized bond line thickness (BLT) measurement. In one embodiment, for example, precision material tester 100 may perform the BLT measurement with an accuracy of ±1.5 µm or better, and a drift of less than 1.5 µm over an extended time frame (e.g., 72 hours) constant BLT test. In one embodiment, this may be accomplished using an inductive sensor having a sensor precision of approximately 0.6 µm, and performing in-situ calibration operations using Z-wedge stage with encoder 122.

In various embodiments, precision material tester 100 may utilize a high precision loading device such as a computer controlled Z-wedge stage with encoder 122. The use of a computer controlled Z-wedge stage with encoder 122 provides a more accurate and consistent load while reducing or eliminating the hysteresis effects or errors associated with conventional systems, such as a conventional pneumatic system. The computer controlled Z-wedge stage with encoder 122 may also enable in-situ calibration operations to facilitate BLT measurement operations. This may be accomplished, for example, using a Z-wedge stage with encoder 122 that is controllable to approximately ±0.1 lbs, and provides a positional accuracy of approximately 0.1 µm. The latter parameter may be particularly useful when performing in-situ BLT sensor calibration operations, for example.

In various embodiments, precision material tester 100 may include a calibration module 126. Calibration module 126 may be arranged to set zero bond line thickness or zeroing operations, and inductive sensor calibration operations for precision material tester 100. Each set of operations may be described with reference to FIGS. 3 and 4 as addressed further below.

Sensor calibration operations may be further improved by performing in-situ calibration at operating conditions. Performing in-situ calibration at operating conditions is typically superior to performing calibrations at room temperature. In one embodiment, for example, anvils 112, 116 may be set to the desired operating temperatures prior to performing calibration operations. As a result, much of the error introduced by the thermal expansion of the sensor mounting brackets may be reduced or eliminated. In this manner, higher degrees of accuracy and lower sensor drift may be achieved using the various in-situ calibration techniques described herein, or other calibration techniques.

In various embodiments, a unique assembly technique may be used when assembling or manufacturing precision material tester 100 in order to provide a higher level of parallelism between the co-planar surfaces of anvils 112, 116. In order reduce measurement errors, the co-planar surfaces of anvils 112, 116 should be substantially parallel to each other. To accomplish this design goal, the surfaces of anvils 112, 116 may be brought together by "ringing," or sliding the flat surfaces against one another to bring the surface into flat, flush contact with each other during assembly. Anvil alignment features 106a, 106b may be arranged as a ball/socket joint. For example, an upper anvil alignment feature 106a may include a receiving socket formed to receive a ball portion disposed on a surface of a lower anvil alignment feature 106b. A layer of bonding material such as epoxy may be applied to the ball portion of lower anvil alignment feature 106b. A release layer of silicon may be applied to the ball portion prior to applying the bonding layer in case of errors incurred during the bonding process. In the event of such errors, the release layer may allow the removal of the bonding layer in order to allow another assembly attempt. Upper anvil alignment feature 106a may then be squeezed together with lower anvil alignment feature 106b to form a small gap of bonding material between the ball portion and the receiving socket and held until the bonding material has cured. Once the bonding material has cured, the co-planar surfaces of anvils 112, 116 will remain flush for subsequent loading and testing operations.

In various embodiments, precision material tester 100 may utilize X-Y stage 104 in order to adjust positions for anvil 112. To perform more accurate measurements it may be important to align the central axes of anvils 112, 116. X-Y stage 104 may be used to move anvil 112 in order to correct any axial misalignment of anvils 112, 116. X-Y stage 104 may move anvil 112 until both anvils 112, 116 are axially aligned. This may reduce or eliminate any systemic errors during assembly operations. For example, a co-axial alignment error of as little as 0.25 mm may increase the measurement error to unacceptable levels. X-Y stage 104 allows for precise adjustment of anvil 112 relative to 116 to reduce or eliminate such errors. Such adjustments may be made before, during or after assembly of precision material tester 100. This provides superior results over conventional techniques, which typically rely upon mechanical adjustments performed during the manufacturing process.

In various embodiments, precision material tester 100 determines heat flux analytically from the improved temperature gradient as measured using the multiple (e.g., six) thermistors implemented for each of anvils 112, 116. As a result, the heat flux measurement is more accurate than other conventional techniques since it accounts for convective losses on anvils 112, 116. Precision material tester 100 may determine the heat flux in accordance with Equation (2) as follows:

$$q = -kA\ dT/dx \qquad \text{Equation (2)}$$

where q=heat transfer rate (heat flow) in Watts, Q=heat flux or heat transfer rate per unit area (Watts/m$^2$), Θ=thermal resistance (° C.-cm$^2$/W), T=temperature (° C.), k=thermal conductivity (W/ m-° C.), A=cross sectional area of anvil (m$^2$), and dT/dx=slope of the anvil temperature profile at position x. For a linear fit (T(x)=mx+b) of the 6 measured data points, the slope (dT/dx=m) is the same value at all values of x. For a polynomial fit (T(x)=ax$^2$+bx+c) of the 6 measured data points, the slope (dT/dx=2ax+b) is different at all positions, x, along the length of the anvil.

Figure 2:
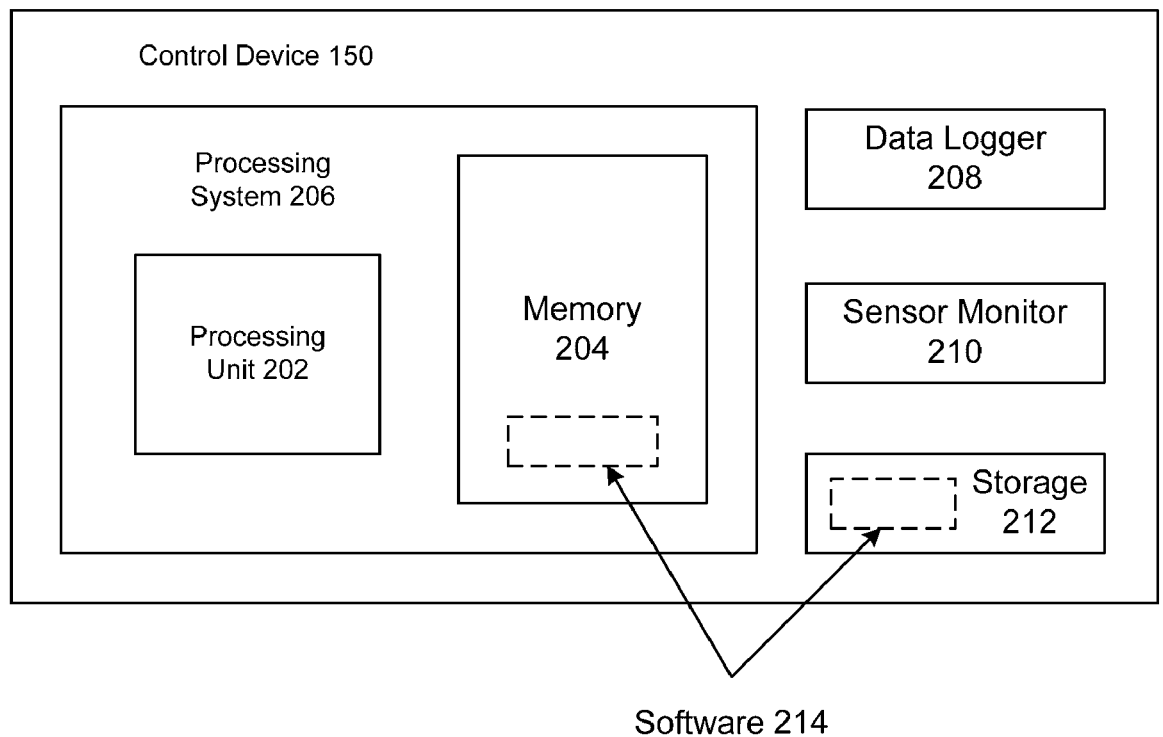
FIG. 2 illustrates one embodiment of a controller.

FIG. 2 illustrates one embodiment of a control device. FIG. 2 illustrates a more detailed block diagram for control device 150 as used with precision material tester 100. As shown in FIG. 2, control device 150 may comprise multiple elements, such as a processing system 206 having a processor 202 and a memory 204, a data logger 208, a sensor monitor 210, storage 212, and one or more software programs 214. The embodiments, however, are not limited to the elements shown in this figure.

In various embodiments, control device 150 may include a processor 202. Processor 202 may be implemented as any processor, such as a complex instruction set computer (CISC) microprocessor, a reduced instruction set computing (RISC) microprocessor, a very long instruction word (VLIW) microprocessor, a processor implementing a combination of instruction sets, or other processor device. In one embodiment, for example, processor 202 may be implemented as a general purpose processor, such as a processor made by Intel Corporation, Santa Clara, Calif. Processor 202 may also be implemented as a dedicated processor, such as a controller, microcontroller, embedded processor, a digital signal processor (DSP), a network processor, a media processor, an input/output (I/O) processor, and so forth. The embodiments are not limited in this context.

In various embodiments, control device 150 may include a memory 204. Memory 204 may include any machine-readable or computer-readable media capable of storing data, including both volatile and non-volatile memory. For example, memory 204 may include read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, or any other type of media suitable for storing information. It is worthy to note that some portion or all of memory 204 may be included on the same integrated circuit as processor 202, or alternatively some portion or all of memory 204 may be disposed on an integrated circuit or other medium, for example a hard disk drive, that is external to the integrated circuit of processor 202. The embodiments are not limited in this context.

Control device 150 may also have additional features and/or functionality beyond processing system 206. For example, control device 150 may include storage 212, which may comprise various types of removable or non-removable storage units. Storage 212 may be implemented using any of the various types of machine-readable or computer-readable media as previously described. Control device 150 may also have one or more input devices (e.g., a keyboard, mouse, pen, voice input device, touch input device, and so forth), one or more output devices 216 (e.g., a display device, speakers, printer, and so forth), and one or more communication connections (e.g., wireless transceiver, network interface card, wireless and/or wireless connectors, and so forth) as well.

In various embodiments, control device 150 may further include various sensing and data acquisition elements. For example, control device 150 may include a data logger 208. In one embodiment, for example, the data logger may be implemented as an Agilent Model 34970A data logger. In another example, control device 150 may include sensor monitor 210. Sensor monitor 210 may be implemented using a computer-based A/D card. In operation, sensor monitor 210 may sample signals from TEC and load cell 118 and inductive position sensor 114.

As shown in FIG. 2, memory 204 and/or storage 212 may be used to store various software programs 214. In one embodiment, for example, software programs 214 may include software programs to implement one or more controllers 130-1-*m* and accompanying data. Software programs 214 may also include control module 128 that may allow the user set test parameters, initiate a test, and monitor the progress of a test. While a test is in progress, the control module 128 automatically maintains the test parameters supplied by the user, collects data, performs real time analysis and stores relevant test data on a computer hard disk. Software programs 214 may further include a calibration module 126 to calibrate precision material tester 100 prior to performing testing operations. Calibration module 126 and/or control module 128 may be further described with reference to FIG. 3.

Operations for the above embodiments may be further described with reference to the following figures and accompanying examples. Some of the figures may include a logic flow. Although such figures presented herein may include a particular logic flow, it can be appreciated that the logic flow merely provides an example of how the general functionality as described herein can be implemented. Further, the given logic flow does not necessarily have to be executed in the order presented unless otherwise indicated. In addition, the given logic flow may be implemented by a hardware element, a software element executed by a processor, or any combination thereof. The embodiments are not limited in this context.

Figure 3:
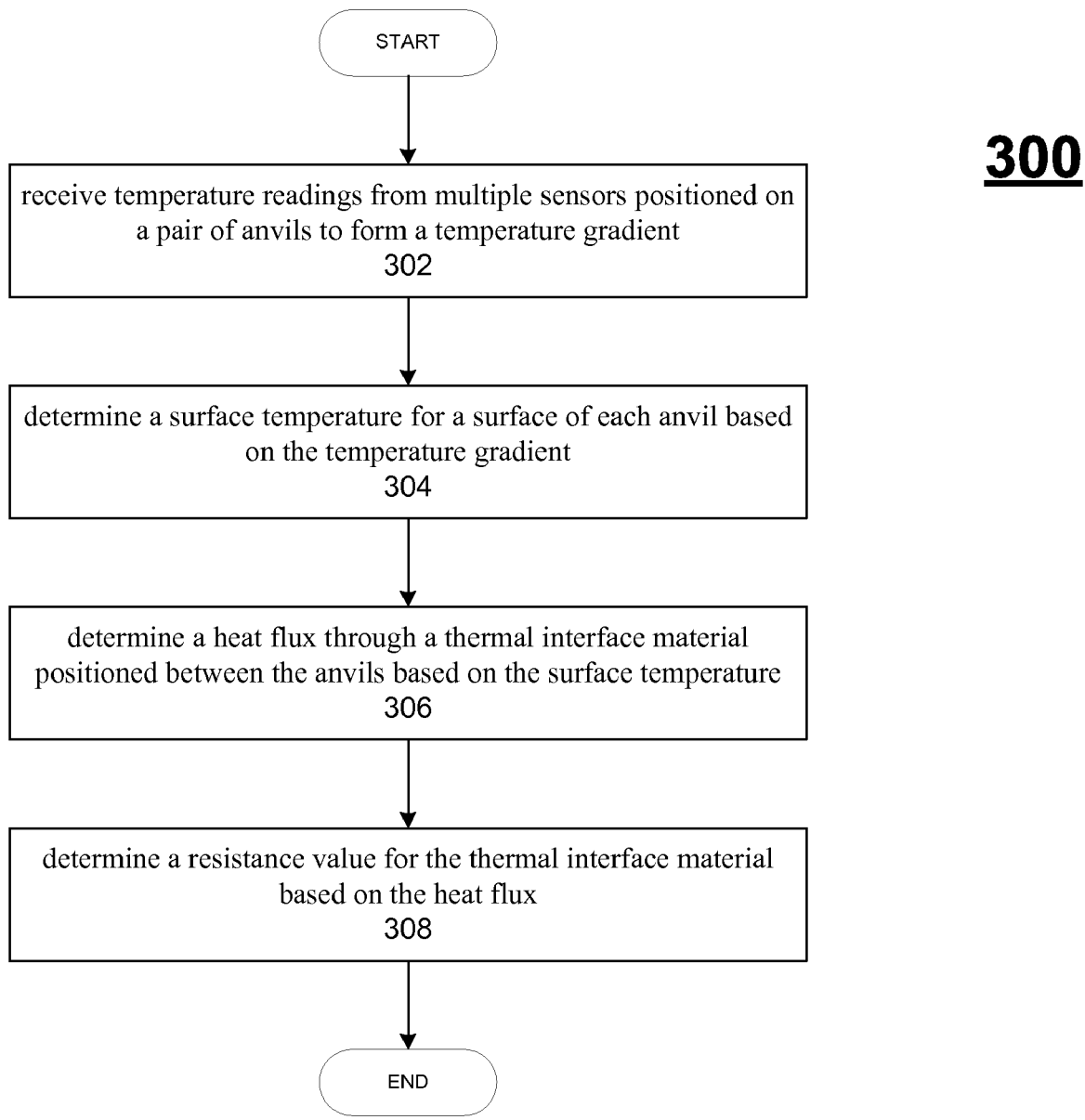
FIG. 3 illustrates one embodiment of a first logic diagram.

FIG. 3 illustrates one embodiment of a logic flow. FIG. 3 illustrates a logic flow 300. Logic flow 300 may be representative of the operations executed by one or more embodiments described herein, such as calibration module 126 and/or control module 128 for precision material tester 100. As shown in logic flow 300, temperature readings may be received from multiple sensors positioned on a pair of anvils to form a temperature gradient at block 302. A surface temperature may be determined for a surface of each anvil based on the temperature gradient at block 304. A heat flux through a thermal interface material positioned between the anvils may be determined based on the surface temperature at block 306. A resistance value for the thermal interface material may be determined based on the heat flux at block 308. The embodiments are not limited in this context.

In one embodiment, for example, loading the thermal interface material between the anvils may be accomplished using a computer controlled Z-wedge with encoder. The embodiments are not limited in this context.

In one embodiment, for example, signals may be received from an inductive sensor. A bond line thickness may be measured based on the received signals. The embodiments are not limited in this context.

In one embodiment, for example, one of the anvils may be heated to operating temperature. The sensors may be calibrated once the heated anvil is heated to the proper operating temperature. The embodiments are not limited in this context.

As previously described, calibration module 126 for precision material tester 100 may be arranged to set zero bond line thickness or zeroing operations, and inductive sensor calibration operations for precision material tester 100. Each set of operations may be described with reference to FIGS. 4 and 5.

Figure 4:
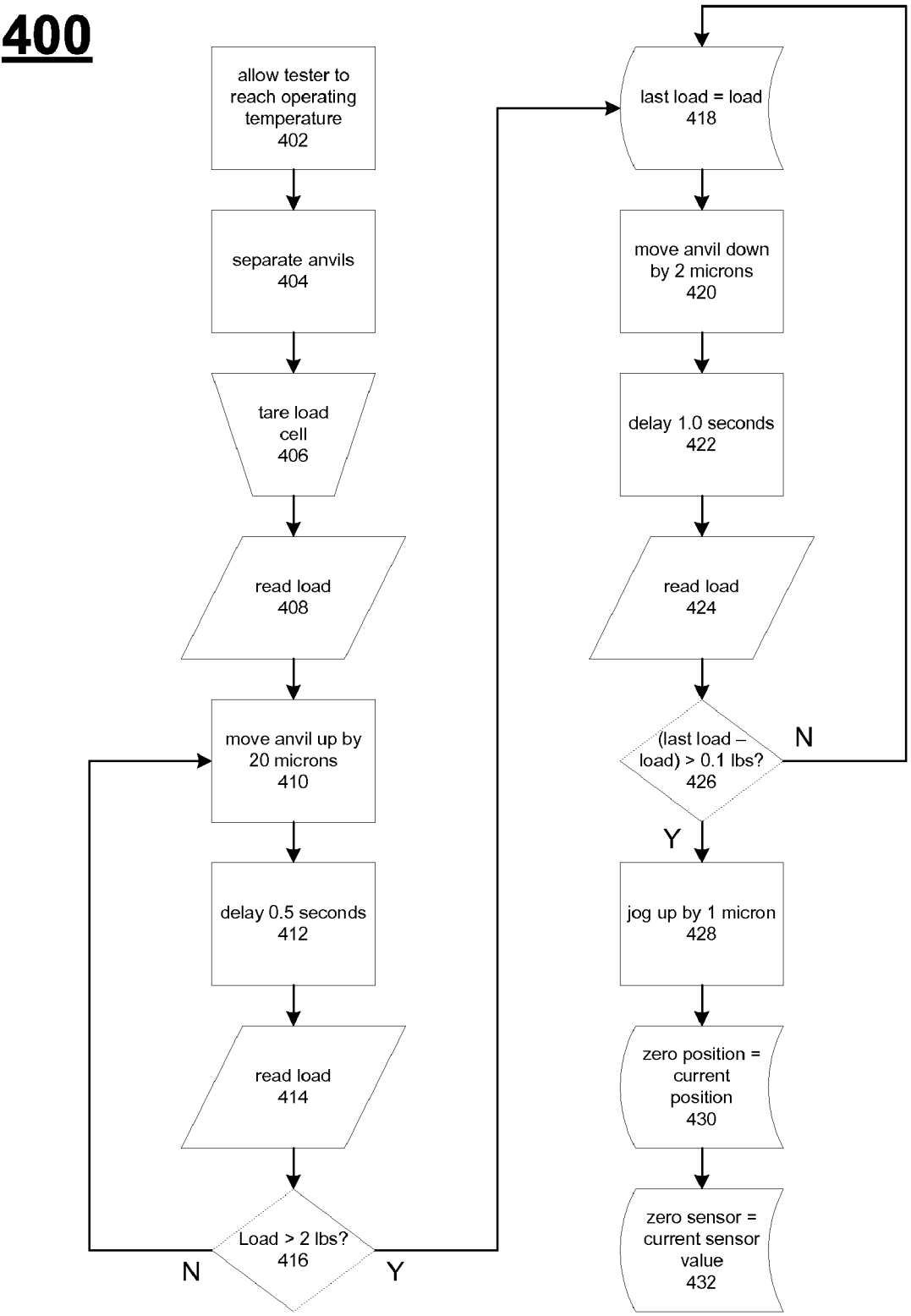
FIG. 4 illustrates one embodiment of a second logic diagram.

FIG. 4 illustrates one embodiment for zeroing operations to set zero bond line thickness for precision material tester 100. The zeroing operations may be performed by, for example, calibration module 126. As shown in FIG. 4, precision material tester 100 may be allowed to reach operating temperature at block 402. Anvils 112, 116 may be separated at block 404. Tare load cell operations may be performed at block 406 manually, or some cases, automatically. The load may be read at block 408. Anvil 112 and/or anvil 116 may be moved up by approximately 20 microns at block 410. A delay of 0.5 seconds may be introduced at block 412. The load may be read at block 414. If the load is not greater than 2 lbs at diamond 416, then control is passed to block 410 to repeat operations. If the load is greater than 2 lbs at diamond 416, however, then the last load is set to the load at block 418. Anvil 112 and/or anvil 116 may be moved down by approximately 2 microns at block 420. A delay of 1.0 seconds may be introduced at block 422. The load is read at block 424. If the last load minus the load is less than 0.1 lbs, then control is passed to block 418 to repeat operations. If the last load minus the load is greater than 0.1 lbs, however, then jog up by 1 micron at block 428. The zero position is set equal to the current position at block 430. The zero sensor may be set to the current sensor value at block 432.

Figure 5:
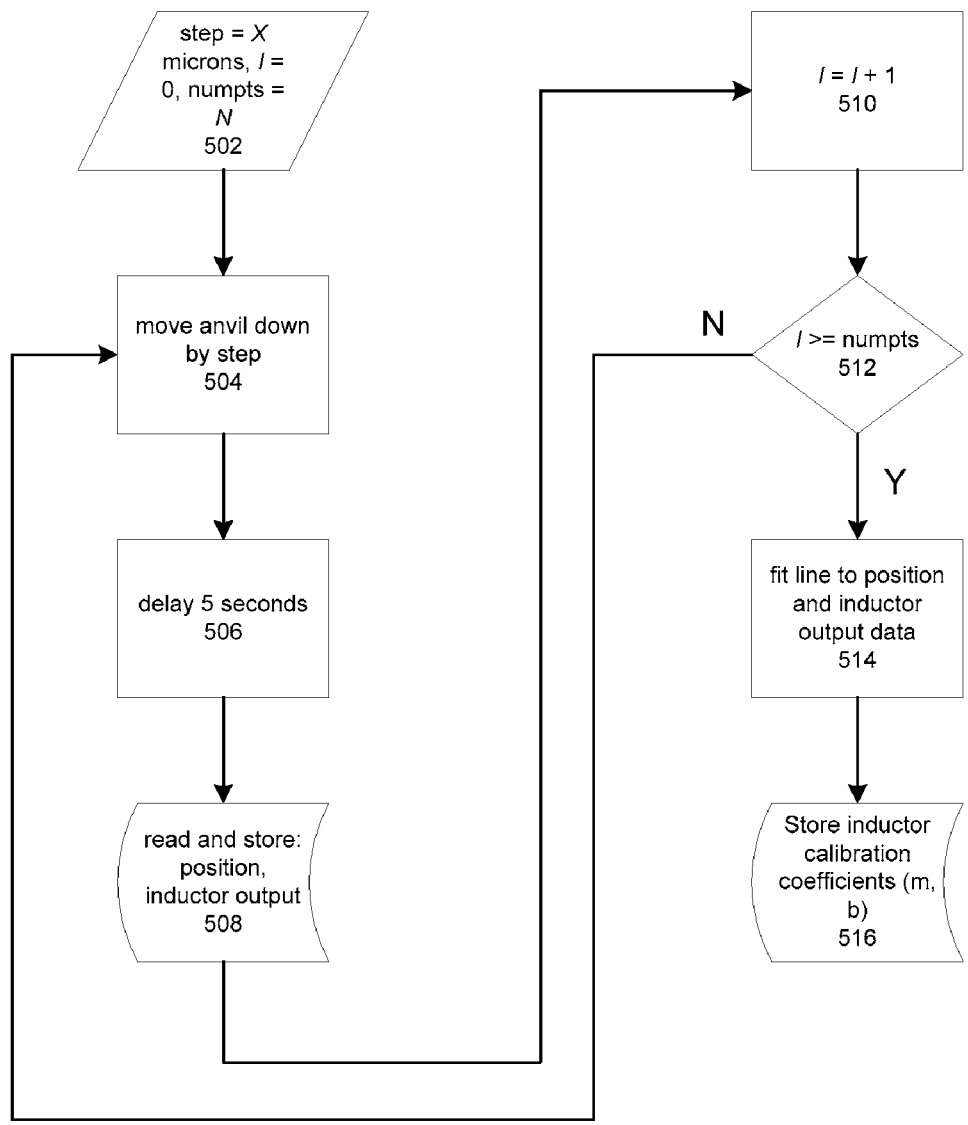
FIG. 5 illustrates one embodiment of a third logic diagram.

FIG. 5 illustrates one embodiment of sensor calibration operations for precision material tester 100. The sensor calibration operations may be performed by, for example, calibration module 126. As shown in FIG. 5, the variables Step may be set to X microns, I may be set to 0, and numpts may be set to N at block 502. Anvil 112 and/or anvil 116 may be moved down by Step at block 504. A delay of approximately 5 seconds may be introduced at block 506. Values for position and inductor output may be read and stored at block 508. The variable I may be incremented by 1 at block 510. If I is less than numpts at diamond 512, control may be passed to block 504 to repeat operations. If I is greater than or equal to numpts at diamond 512, however, then the line may be fit to position and inductor output data at block 514. The inductor calibration coefficients (m, b) may be stored at block 516.

Numerous specific details have been set forth herein to provide a thorough understanding of the embodiments. It will be understood by those skilled in the art, however, that the embodiments may be practiced without these specific details. In other instances, well-known operations, components and circuits have not been described in detail so as not to obscure the embodiments. It can be appreciated that the specific structural and functional details disclosed herein may be representative and do not necessarily limit the scope of the embodiments.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. An apparatus, comprising:
   a hot anvil and a cold anvil each having multiple sensors disposed along its axis;
   a thermal interface material disposed between said anvils;
   an inductive sensor disposed on one of said anvils to perform bond line thickness measurements; and
   a control module to communicatively couple to said sensors, said control module arranged to receive temperature readings from said multiple sensors to form a temperature gradient, determine a surface temperature for each anvil based on said temperature gradient, determine a heat flux through said thermal interface material based on said surface temperature, and determine a resistance value for said thermal interface material based on said heat flux.

2. The apparatus of claim 1, said hot anvil and said cold anvil to create said temperature gradient.

3. The apparatus of claim 1, comprising an X-Y stage coupled to one of said anvils, said X-Y stage to move said anvil until both anvils are axially aligned.

4. The apparatus of claim 1, comprising a Z-wedge with encoder to move one of said anvils and to apply a load to said thermal interface material between said anvils upon contact with said thermal interface material.

5. A system, comprising:
   a hot anvil having multiple sensors disposed along its axis;
   a heater block to couple to said hot anvil and heat said hot anvil;
   a cold anvil having multiple sensors disposed along its axis;
   an inductive sensor disposed on one of said anvils to perform bond line thickness measurements;
   a thermoelectric cooler or fan and heat sink unit to couple to said cold anvil and cool said cold anvil;
   a thermal interface material disposed between said anvils; and
   a control device having a control module, said control module to receive temperature readings from said multiple sensors to form a temperature gradient, determine a surface temperature for each anvil based on said temperature gradient, determine a heat flux through said thermal interface material based on said surface temperature, and determine a resistance value for said thermal interface material based on said heat flux.

6. The system of claim 5, said control device having a cooling source controller to communicatively couple to said thermoelectric cooler to control said cooling, and a heating source controller to communicatively couple to said heater block to control said heating.

7. The system of claim 5, comprising a Z-wedge with encoder to load said thermal interface material between said anvils, said control device having a motion controller to communicatively couple to said Z-wedge with encoder to control said load.

8. The system of claim 5, said control device having a calibration module to calibrate said sensors to an accuracy of approximately 1.5 µm.

9. The system of claim 5, comprising:
   a Z-wedge with encoder to load said thermal interface material between said anvils, said control device having a motion controller to communicatively couple to said Z-wedge with encoder to control said load; and
   said control device having a calibration module to calibrate said inductive sensor to an accuracy of approximately 1.5 µm.

10. A method, comprising:
    receiving temperature readings from multiple sensors positioned on a pair of anvils to form a temperature gradient;
    determining a surface temperature for a surface of each anvil based on said temperature gradient;
    determining a heat flux through a thermal interface material positioned between said anvils based on said surface temperature;
    determining a resistance value for said thermal interface material based on said heat flux;
    receiving signals from an inductive sensor; and
    measuring a bond line thickness based on said signals.

11. The method of claim 10, comprising loading said thermal interface material between said anvils using a computer controlled Z-wedge with encoder.

12. The method of claim 10, comprising calibrating said inductive sensor to measure a bond line thickness.

13. The method of claim 11, comprising:
    calibrating said inductive sensor;
    heating one of said anvils to an operating temperature;
    cooling one of said anvils to an operating temperature; and
    calibrating said inductive sensor once said anvils are at said operating temperatures.

14. An article comprising a machine-readable storage medium containing instructions that if executed enable a system to:
    receive temperature readings from multiple sensors positioned on a pair of anvils to form a temperature gradient;
    determine a surface temperature for a surface of each anvil based on said temperature gradient;
    determine a heat flux through a thermal interface material positioned between said anvils based on said surface temperature;
    determine a resistance value for said thermal interface material based on said heat flux;
    receive signals from an inductive sensor; and measure a bond line thickness based on said signals.

15. The article of claim 14, further comprising instructions that if executed enable the system to load said thermal interface material between said anvils using a computer controlled Z-wedge with encoder.

16. The article of claim 14, further comprising instructions that if executed enable the system to:
    receive signals from said inductive sensor;
    heat one of said anvils to operating temperature;
    cool one of said anvils to operating temperature; and
    calibrate said inductive sensor once said anvils are at said operating temperatures.

17. The article of claim 14, further comprising instructions that if executed enable the system to calibrate said inductive sensor to measure a bond line thickness.

* * * * *